United States Patent [19]
Gönner

[11] Patent Number: 5,255,725
[45] Date of Patent: Oct. 26, 1993

[54] PROCESS FOR THE ROTARY TRUING OF PLANKS AND THE LIKE

[75] Inventor: Siegmar Gönner, Oberkirch, Fed. Rep. of Germany

[73] Assignee: Gebruder Linck Maschinenfabrik "Gatterlinck" GmbH & Co. KG, Oberkirch, Fed. Rep. of Germany

[21] Appl. No.: 852,231

[22] PCT Filed: Nov. 19, 1990

[86] PCT No.: PCT/EP90/01971

§ 371 Date: Jun. 5, 1992

§ 102(e) Date: Jun. 5, 1992

[87] PCT Pub. No.: WO91/08878

PCT Pub. Date: Jun. 27, 1991

[30] Foreign Application Priority Data

Dec. 8, 1989 [DE] Fed. Rep. of Germany ....... 3940614

[51] Int. Cl.[5] .................................. B27B 1/00
[52] U.S. Cl. ............................ 144/356; 100/155 R; 100/176; 144/2 R; 144/255; 144/246 R; 144/359; 144/362; 364/559
[58] Field of Search ............... 144/2 R, 255, 333, 356, 144/357, 362, 361, 359; 100/155 R, 160, 176; 156/209, 220; 250/223 R, 560, 562, 563, 572; 364/507, 559

[56] References Cited

U.S. PATENT DOCUMENTS 4,503,892 3/1985 Gönner .
4,977,940 12/1990 Gönner et al. .

FOREIGN PATENT DOCUMENTS 3623235 1/1988 Fed. Rep. of Germany .
60-242355 2/1985 Japan .
255459 9/1946 Switzerland .

*Primary Examiner*—W. Donald Bray
*Attorney, Agent, or Firm*—Burns, Doane, Swecker & Mathis

[57] ABSTRACT

Wooden boards which are deformably twisted about their longitudinal axes are straightened by being passed through a path that is twisted in a direction opposite that of the boards. The degree of twist of the boards is automatically adjusted as a function of the humidity of the boards and possibly also as a function of the temperature of the boards.

9 Claims, 4 Drawing Sheets

PROCESS FOR THE ROTARY TRUING OF PLANKS AND THE LIKE

BACKGROUND OF THE INVENTION

The invention concerns a process for the rotary truing of planks and the like around their longitudinal axes by means of a plank guide channel through which the planks pass in the longitudinal direction, said channel having a twist around the longitudinal axis which is variable by adjusting the parts forming the plank guide channel.

In the case of a known straightening apparatus (DE-B-32 07 548), planks and in particular planks cut from the sides of a flattened tree trunk by a chipless cutting method are straightened, together with similar flat wood products such as plates with a curvature around a transverse axis, between rolls.

However, primarily the boards or the like (also designated plates) produced by the chipless method described frequently exhibit in addition to the abovementioned curvature a twist, i.e. they are twisted or turned around their longitudinal axis. This deformation in numerous applications prevents any automatic further processing of the boards. The twist increases with the angle of inclination of the board-cutting blades with respect to the longitudinal direction of the trunk.

A known process of the abovementioned generic type (DE-A-37 01 127) is used to straighten the boards produced. For the purpose, the boards pass through a board guide channel with a spiral distortion, i.e. a twist around its longitudinal axis. In this manner, the boards are given a continuous twist in the course of their passage in a direction opposite to their original twist. In the process, the boards are straightened so that they then have a permanent straight shape.

The individual parts forming the board guide channel, for example pairs of rolls, may be pivoted, so that a more or less intensive twist of the board guide channel may be set as a function of the straightening effect required. It is possible in this fashion to adapt the known process as needed. The adjustment of the board guide channel is carried out in accordance with empirical values primarily as a function of the twist present in the untreated boards. If the boards still have twists after passing through the board guide channel, the setting of the board guide channel is altered until a satisfactory result is obtained. These adjustment activities are very expensive, mainly because the initial state of the boards varies frequently and because the physical and chemical properties of the wood also have a significant effect.

It is further known (DE-A-36 23 235), to utilize the humidity of the wood to regulate a processing parameter in the chipless cutting of boards from a tree trunk. In this process the measured value of the humidity of the wood is used to vary the contact pressure of a pressure beam which applies pressure to the point at which the boards are cut. No straightening process is involved.

SUMMARY OF THE INVENTION

It is therefore the object of the present invention to develop a process of the aforementioned generic type so that—beginning with an initial setting—automatic adaptation to the varying properties of the wood is possible.

This object is attained according to the invention by measuring the humidity of the wood to be straightened and varying the twist the board guide channel as a function of the humidity of the wood.

It was discovered surprisingly for the first time that the humidity of the wood has a decisive effect on the straightening deformation required to equalize a given twist.

The initial setting of the board guide channel is preselected according to the twist of the untreated boards to be straightened and corrected if necessary, after a few test runs so that a straight board is produced. If during the continuing operation there are variations in the humidity of the wood, the setting of the board guide channel may be corrected so that essentially straight boards are obtained in spite of the variation of the humidity of the wood.

According to an advantageous embodiment of the concept of the invention the wood temperature of the board to be straightened is also measured and the twist of the board guide channel is varied as a function of the wood temperature measured.

It was found further that the effects of the humidity and the temperature of the wood on the resulting twist of the boards or other wood products cannot be determined in a satisfactory manner by empirically ascertaining the twist of the board guide channel. The wood to be processed in most cases does not have a continuously uniform humidity and/or temperature. Rather, these values may vary in many cases over the length of the wood. The cause of this is to be found in the fact that the wood is usually stored prior to processing in large stacks. In most cases the humidity and temperature have different values inside the stack and in the outer areas. These findings are valid for stacks of wood exposed outdoors to the whether, but also for stacks brought to higher temperatures and humidities in conditioning chambers prior to processing. This conditioning is favorable for the subsequent chipless cutting of boards and is therefore applied preferably. However, it causes significant differences in the humidity and/or the temperature of the wood, leading to different twists of the board produced that must be equalized by a straightening process.

Only by means of the continuous determination of the humidity and temperature of the wood and the continuous variation of the twist of the board guide channel as a function of this determination is it possible to control the straightening process so that even under the aforementioned aggravating conditions an adequately straight board may be produced.

If an increase in the humidity and/or temperature of the wood is observed, the twist of the wood guide channel is reduced. If, on the other hand, both of one of these values declines, the twist of the wood guide channel is increased.

The invention provides for that the variation of the twist of the wood guide channel is carried out additionally as a function of the feed rate, the type and the width of the wood and/or the thickness of the board. The temperature and/or the humidity of the wood may be measured prior to the entry of the boards in the wood guide channel or after its exit from said channel.

BRIEF DESCRIPTION OF THE DRAWINGS

In the following, examples of the embodiment of the invention are explained in more detail, with reference to the drawing, wherein.

DETAILED DESCRIPTION OF PREFERRED EMBODIMENTS OF THE INVENTION

Figure 1:
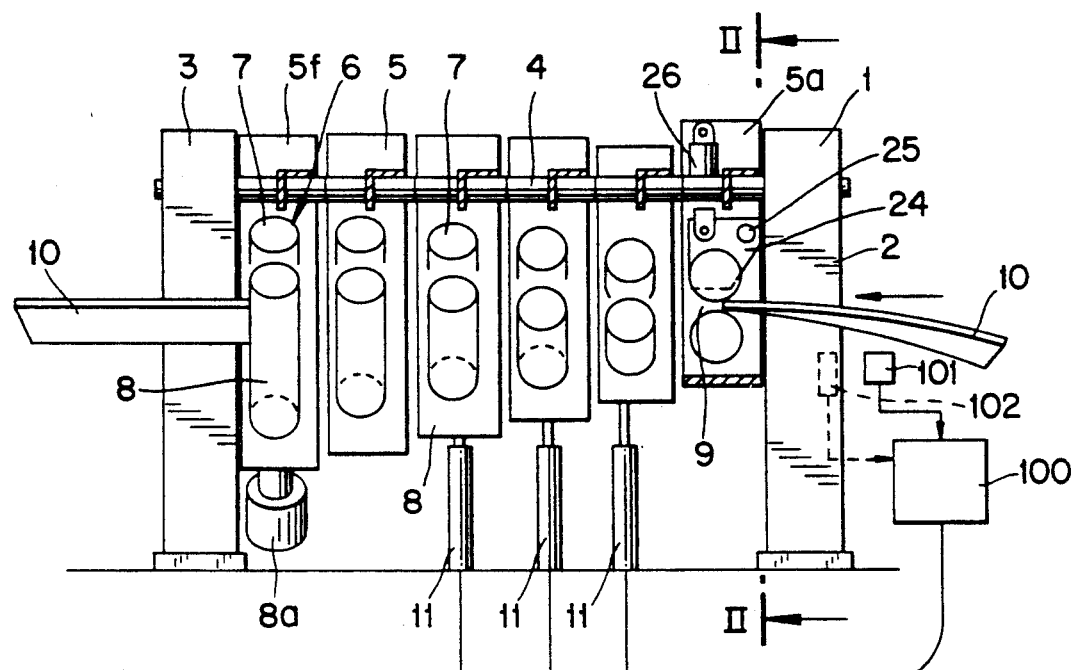
FIG. 1 shows an apparatus for the straightening of boards in a simplified view in a lateral elevation and in a partial longitudinal section, FIG. 2 a section on the line II—II in FIG. 1, FIG. 3 a simplified top elevation of the apparatus according to FIG. 1 to 3, FIG. 4 in a view corresponding to FIG. 1 a modified form of embodiment of the apparatus, FIG. 5 a section on the line V—V of FIG. 4, FIG. 6 in a lateral elevation and in a partial section another form of embodiment of an apparatus according to the invention and FIG. 7 a section on the line VII—VII in FIG. 6.
Figure 2:
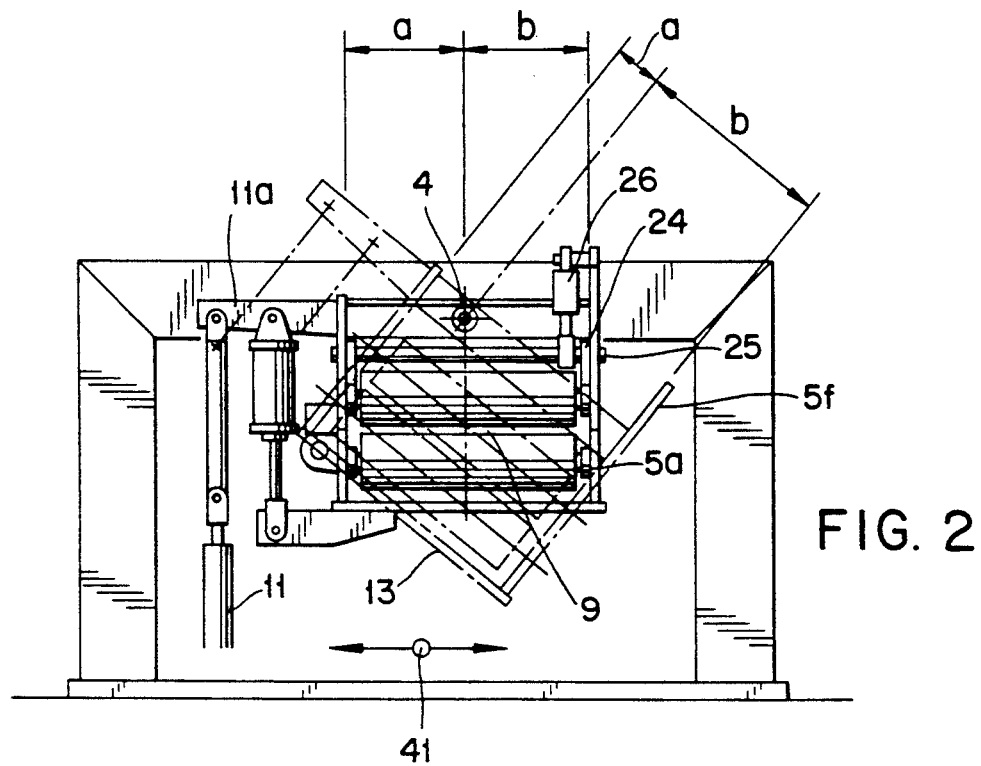
Figure 3:
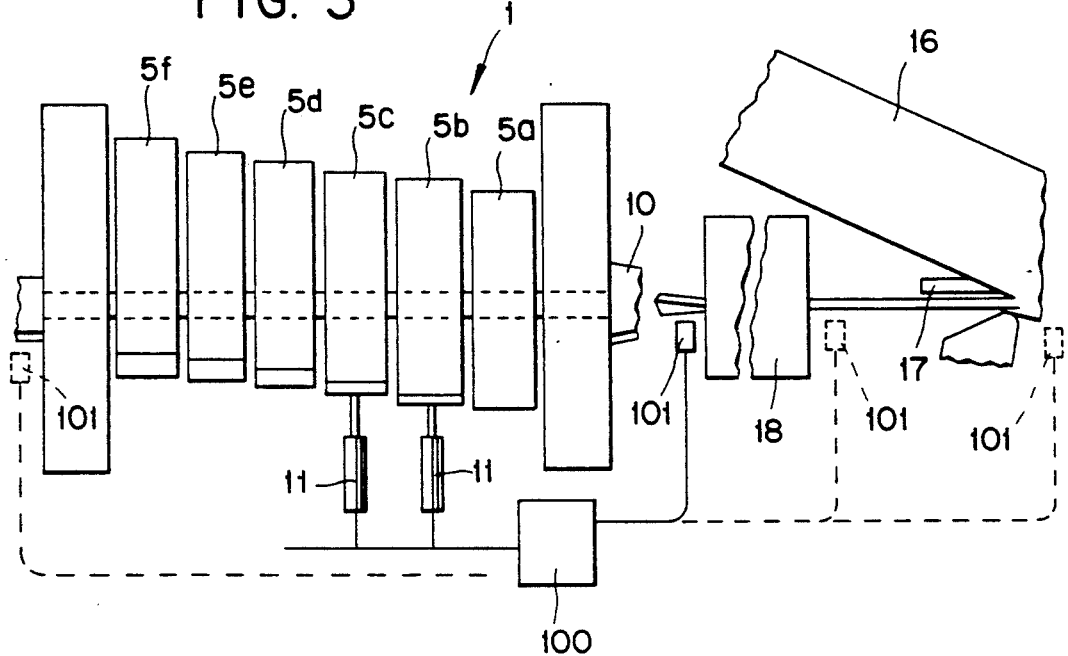

The apparatus shown in FIG. 1 to 3 comprises a frame 1 consisting essentially of two gantry like supports 2 and 3 mounted in succession to each other at the inlet and outlet of the apparatus, and an axle 4 extending in the longitudinal direction of the frame and connecting the two supports 2, 3.

The axle 4 forms a pivoting axle for a plurality of roller stands 5, in particular, stands 5a-5f (see FIG. 3), following each other in succession and each comprising a pair 6 of rollers, consisting of an upper roller 7 and a lower roller 8, located parallel to and spaced apart from said upper roller.

In FIG. 2 an initial roller stand 5a is shown with normal lines. A final roller stand 5f located at the outlet of the frame is indicated by thin lines in FIG. 2. It is seen that the roller stand 5f is angled relative to the roller stand 5a around the axle 4. It is further seen that the pivoting axle 4 is centered in the first roller stand 5a, i.e. the dimensions a and b of the stand 5a located on opposite sides of the axle 4 are equal. In the roller frame 5 the pivoting axle 4 is eccentric, i.e. the dimension a is significantly smaller than the dimension b. In a similar manner, all of the roller frames 5 are angled or staggered relative to the preceding stands by a certain angle around the longitudinal axis of the frame. This creates between the rollers 7, 8 a board guide channel 9 (FIG. 2) extending in the longitudinal direction of the frame and having a twist over its entire length. The boards 10 (FIG. 1) pass through this channel, in their initial state they also have a twist, counter in direction to the twist of the board guide channel 9. Following their passage through the board guide channel 9, the boards 10 exit in the straightened condition, as indicated in FIG. 1.

Each of the roller stands 5 is connected with a pivot drive 11, consisting for example of a pressure cylinder acting on a lateral arm 12 of the roller stand 5.

The pivot drives 11 associated with the individual roller frames 5 are regulated together by means of a control 100 in a manner such that the twist angle of the board guide channel 9 may be varied. For this, the humidity of the wood of the board 10 passing into the board straightening guide is detected by means of a humidity sensor 101 schematically indicated in FIG. 1; this value is communicated to the control device 100. Beginning with an initial setting, which in case of a predetermined wood humidity leads to straightened boards, the board guide channel 9 is adjusted in the direction of a stronger twist, whenever the humidity sensor 101 detects a decline in the humidity of the wood.

As merely indicated in FIG. 1 by broken lines, a temperature sensor 102 may also be provided; it detects the wood temperature of the board to be straightened and again passes the value determined on to the control device 100, so that the adjustment of the twist of the board guide channel 9 may be regulated together or separately as a function of the wood temperature determined. Whenever the temperature sensor 102 detects a decrease in the wood temperature, a larger twist of the board guide channel is set.

At least the roller 8 in each roller stand 5 is equipped with a roller drive 8a toward convey the board 10 to the outlet of the apparatus as depicted in connection with the final stand 5f.

In order to open the board guide channel 9, the lower part 13 of each roller stand 5f and 5a may be swung downwardly (as described in more detail in connection with FIG. 5). Residual wood or board portions which accumulate or become jammed in the board guide channel 9 may be removed simply by swinging the roller stand so that the rollers are vertical, whereupon the residues either drop out or may easily be removed.

FIG. 3 shows in a top elevation the lateral offset of the successive roller stands 5. FIG. 3 also shows that the boards 10 to be straightened in the most important case of application are cut from a laterally flattened log 16 chiplessly by a blade 17. Following their passage through a bending straightening apparatus 18 indicated in FIG. 3 schematically only, wherein their curvature is eliminated, the boards 10 immediately enter the apparatus removing their twist. The magnitude and direction of the twist depend essentially on the inclined setting of the blades 17.

FIG. 3 shows that the humidity sensor 101 may be located between the bending straightening apparatus 18 and the twist straightening apparatus. However—as indicated by broken lines in FIG. 3—the humidity sensor 101 may also be located at the inlet of the boards 10 into the bending straightening apparatus 18 or at the point where the boards are cut chiplessly by the blades 17 from the log 16.

Finally, FIG. 3 indicates that the humidity sensor 101 may also be located at the end of the board guide channel 9 in order to measure the humidity of the wood. The temperature of the wood may also be determined in these locations for the control device 100.

Figure 4:
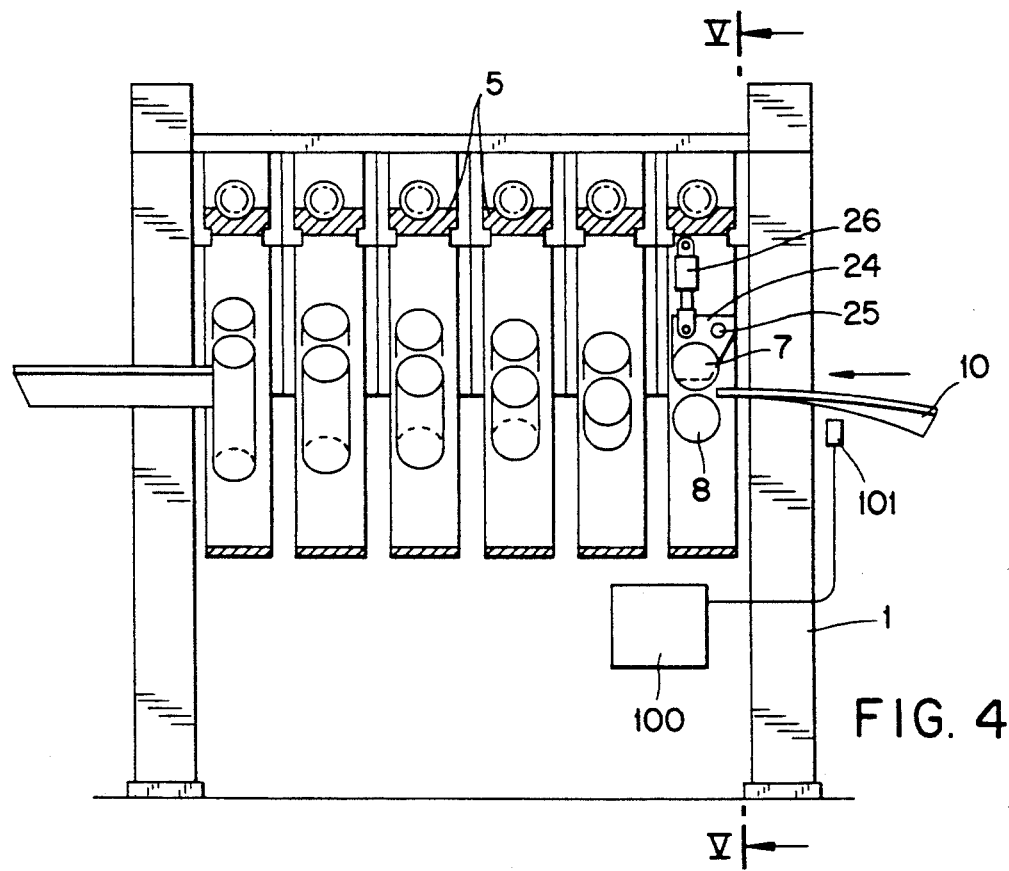
Figure 5:
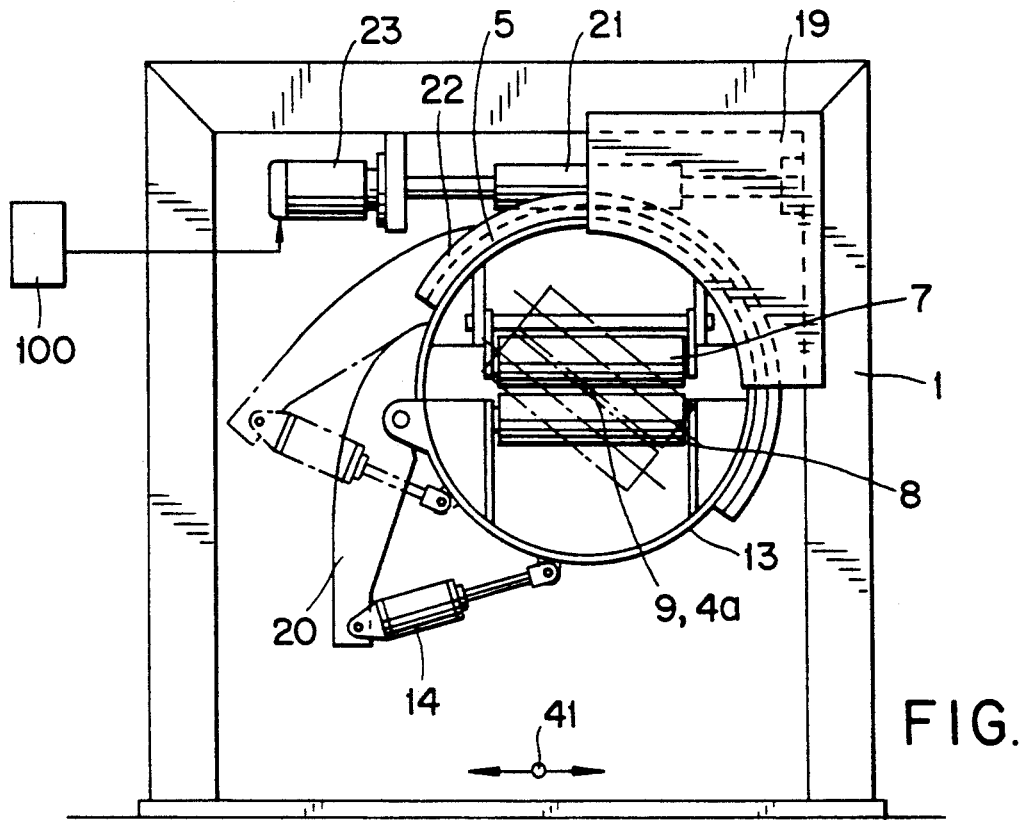

The modified apparatus shown in FIGS. 4 and 5 differs from the apparatus described above and illustrated in FIGS. 1 to 3 essentially only in that the individual successive roller stands 5 may be pivoted around a longitudinal frame axis approximately coinciding with the board guide channel 9. In this case the roller stands form a ring wherein the rollers 7, 8 are bearingly supported. These annular roller stands are moved in a sliding guide in a guide part 19 on a circular path, the center of which is located in the longitudinal axis of the frame.

The roller stand 5 may be opened and closed. A pressure cylinder 14 is acting on the on the lower part 13 of the roller stand in which the roller 8 is located, said pressure cylinder being mounted on an arm 20 connected with the roller stand 5. By actuating the cylinder 14 the roller 8 can be swung up or down relative to the roller 7.

As the pivot drive in the embodiment according to FIGS. 4 and 5 a worm drive 21 is provided;, it drives a worm segment 22 on the annular roller stand 5 by means of a servomotor 23.

A humidity sensor 101 is again provided in the embodiment shown in FIGS. 4 and 5, the output signal of which is passed on to the control device 100. The latter adjusts the servomotors 23 as a function of the humidity and optionally the temperature of the wood, to vary the twist of the board guide channel 9.

For the adjustment to different board thicknesses, in the embodiments according to FIGS. 1 to 5 in each roller stand the upper roller 7 is adjustable relative to the lower roller 8. For this, the upper roller 7 may be pivoted on a lateral support 24 around a pivot axle 25, as depicted only in connection with the initial stand 5a. The pivoting adjustment is effected by means of a pressure cylinder 26.

Figure 6:
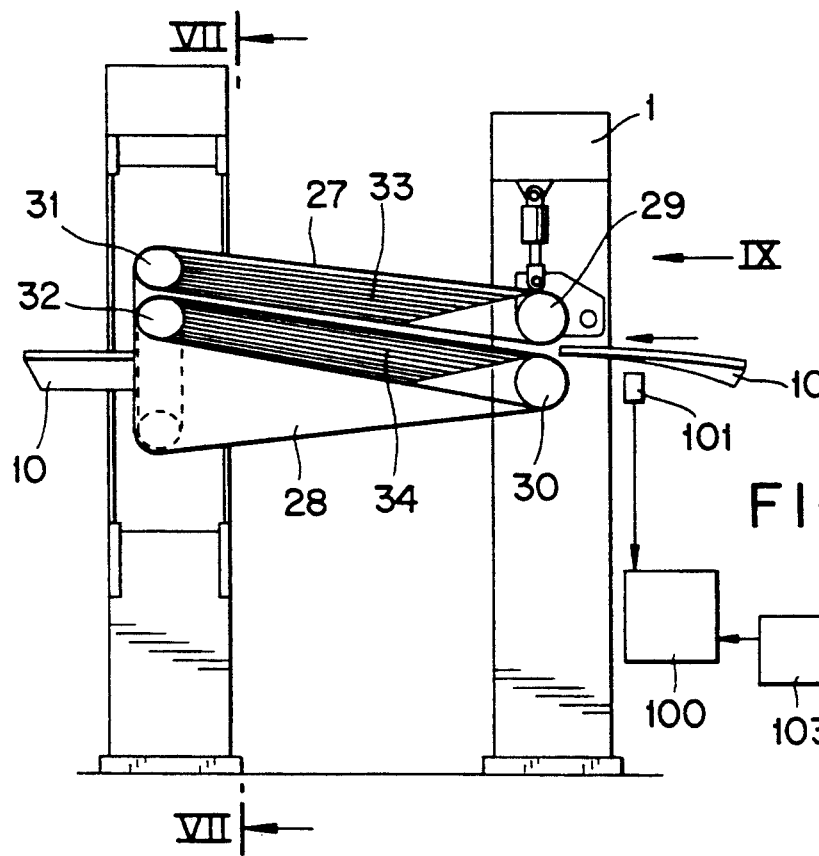
Figure 7:
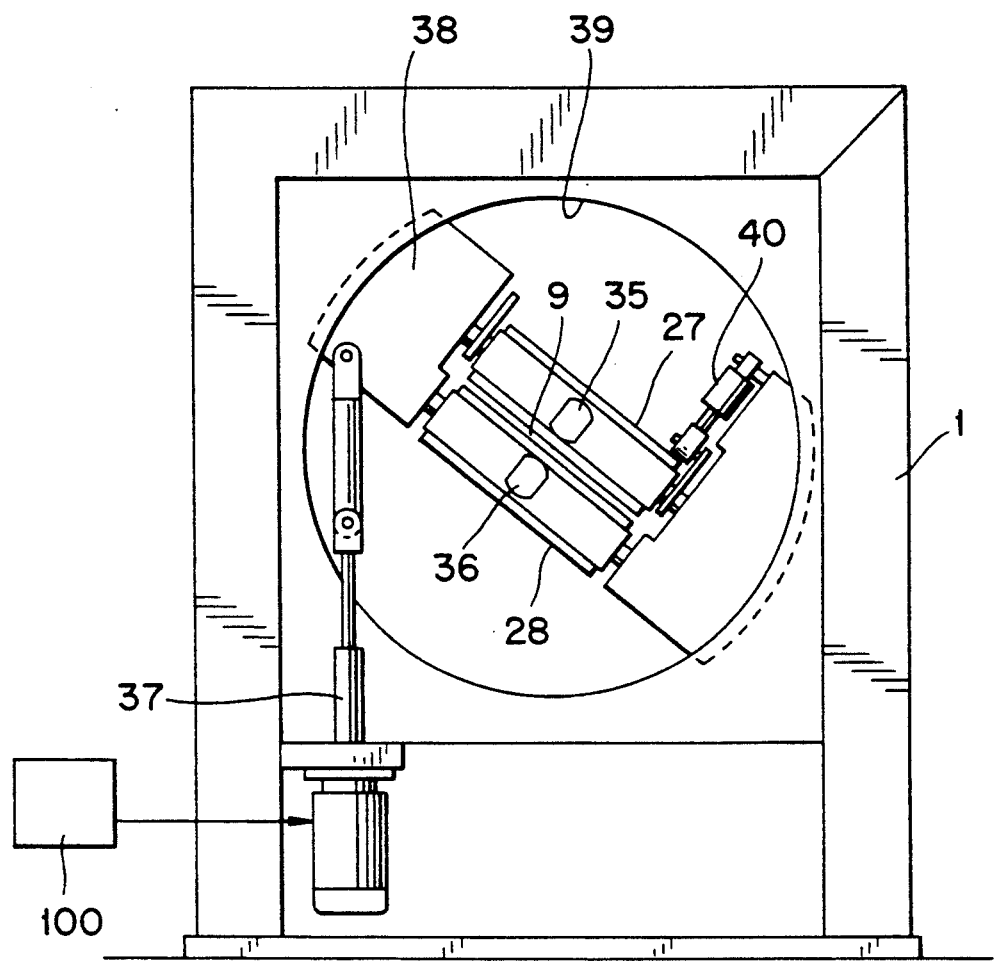

In FIGS. 6 and 7 another form of embodiment of the apparatus is shown. Two conveyor belts 27, 28 extend from an inlet roller pair 29, 30 to an outlet roller pair 31, 32 offset relative to the rollers 29, 30. The two conveyor belts 27, 28 thus exhibit a twist if viewed in their longitudinal direction; they form between them a board guide channel 9 also provided with a twist, through which the board 10 to be straightened is passing. The staggered conveyor belts 27, 28 may be rubber belts with a textile insert or metal link chains or chain belts.

In order to prevent the board 10 passing through the board guide channel 9 from pressing in the center area of the conveyor belts 27, 28 the strands 33, 34 facing each other, apart, preferably in the center range of the conveyor belts 27, 28, crowned support rollers 35, 36 may be located on the reverse side of the strands 33, 34 (FIG. 7). At least one of the two conveyor belts is driven, so that the boards 10 passing through, are completely moved out of the apparatus.

FIG. 7 shows that the roller pair 31, 32 may be pivoted on the outlet side relative to the roller pair 29, 30 on the inlet side, to vary the twist angle of the board guide channel 9 as a function of the prevailing requirements. A pivot drive 37 is used for the purpose; it moves the roller stand, which here is in two parts, on a circular path formed by circular recess 39.

FIGS. 6 and 7 schematically show that here again the values supplied by the humidity sensor 101 of the wood humidity of the boards 10 are processed in the control device 100 in order to regulate the pivot drive 37.

In this form of embodiment an adjusting drive 40 is a gain provided on the two roller parts 29, 30 or 31, 32, making possible in the manner described above the adjustment of the upper rollers 29 and 31, relative to the lower roller 30 and 32 to different board thicknesses.

It is again possible in the form of embodiment according to FIGS. 6 and 7 to make the rollers 30, 32 supporting the lower conveyor belt 28 downward folding, in order to open the board guide channel 9, if broken wood debris must be removed.

It is common to all of the forms of embodiment shown that it is possible to laterally adjust the entire frame 1, as indicated by the arrows 41 in FIGS. 2 and 5.

In the forms of embodiment according to FIGS. 1 to 5, the successively located roller pairs 7, 8 may also be aligned so that curved configuration of the board guide channel 9 is obtained. In this manner, it is possible to straighten the board 10 in its longitudinal direction only, so that a separate straightening apparatus 18 may be eliminated.

FIG. 6 shows an input unit 103 whereby control signals may be entered in the control device 10 as a function of additional values in order to affect the regulation of the board guide channel 9, in particular the feed velocity, the type of wood, the width and the thickness of the board.

I claim:

1. A process for straightening wooden boards which are twisted about their longitudinal axes, comprising the steps of:
   A) displacing said boards along a path of travel which is twisted about a longitudinal axis of said path, the twist direction of the panel being opposite the twist direction of the board, so that the board tends to become straightened as it travels along said path,
   B) measuring the humidity of the boards, and
   C) adjusting the degree of twist of said path as a function of the amount of measured humidity of said boards.

2. A process according to claim 1, wherein step C includes increasing the degree of twist of said path in response to a decline in the amount of measured humidity of said boards.

3. A process according to claim 2 including step D of measuring the temperature of the boards, step C comprising adjusting the degree of twist of said boards as a function of the amounts of measured humidity and temperature of said boards.

4. A process according to claim 3, wherein step C includes increasing the degree of twist of said path in response to a decline of measured temperature of said boards.

5. A process according to claim 1 including step D of measuring the temperature of the boards, step C comprising adjusting the degree of twist of said boards as a function of amounts of measured humidity and temperature.

6. A process according to claim 5, wherein step C includes increasing the degree of twist of said path in response to a decline of measured temperature of said boards.

7. A process according to claim 1 including the step of measuring the feed rate and width of the boards, step C including adjusting the degree of twist of said path as a function of the amounts of measured humidity, feed rate, and width.

8. A process according to claim 7 including the step of measuring the thickness of the boards, step C including adjusting the degree of twist of said path as a function of the amounts of measured humidity, feed rate, width and thickness.

9. A process according to claim 1, including the step of measuring the feed rate and thickness of the boards, step C including adjusting the degree of twist of said path a function of the amounts of measured humidity, feed rate, and thickness.

* * * * *